United States Patent [19]

Oharek

[11] 4,208,107
[45] Jun. 17, 1980

[54] DRUGLESS EYE EXAMINATION SYSTEM

[75] Inventor: Frank J. Oharek, Orlando, Fla.

[73] Assignee: The United States of America as represented by the Secretary of the Navy, Washington, D.C.

[21] Appl. No.: 867,550

[22] Filed: Jan. 6, 1978

[51] Int. Cl.² ............................................. A61B 3/10
[52] U.S. Cl. ........................................ 351/7; 351/16; 351/8
[58] Field of Search ................. 351/6, 7, 8, 9, 13, 351/14, 16; 354/62

[56] References Cited

U.S. PATENT DOCUMENTS

| | | | |
|---|---|---|---|
| 3,454,331 | 7/1969 | Maitenaz | 351/7 |
| 3,533,683 | 10/1970 | Stark et al. | 351/6 |
| 3,925,793 | 12/1975 | Matsumura et al. | 351/7 X |

FOREIGN PATENT DOCUMENTS 1127947 12/1956 France ................................ 351/7

Primary Examiner—John K. Corbin
Assistant Examiner—Rodney B. Bovernick
Attorney, Agent, or Firm—Richard S. Sciascia; Robert W. Adams

[57] ABSTRACT

A drugless eye examination system is disclosed that incorporates: an optical system for illuminating the retina of an eye, which has preferably been previously dilated by standard dark room or other drugless procedures, with infrared energy; another optical system for projecting a tiny red spot light on the retina of said eye, for eye-fixation purposes; and still another optical system for permitting an observer to look at and, hence, examine said eye, while it is being held fixed on said red spot light and illuminated by the aforesaid infrared energy. In combination therewith are several other optical systems which permit the taking of color or other photographs of the retina of said eye while it is optionally and timely illuminated with a flash of white light, and for implementing the remote display thereof by television or other projection apparatus.

5 Claims, 1 Drawing Figure

DRUGLESS EYE EXAMINATION SYSTEM

FIELD OF THE INVENTION

The present invention, in general, relates to optical instruments and, in particular, pertains to optical measuring and testing instruments. In even greater particularity, the subject invention comprises an improved method and means for examining human eyes—and especially the retinas thereof—without using pupil dilation drugs or other medication of any kind.

DESCRIPTION OF THE PRIOR ART

Heretofore, numerous optical instruments have been employed to test human eyes for various and sundry reasons. For example, there are ophthalmoscopic examination instruments, as evidenced by the Method and System for Taking Photographs of an Eye Fundus described in U.S. Pat. No. 3,614,214 to Eilers and Crane, which discloses an instrument for photographing an eye fundus in which a camera having a focus control is aligned with the position of an eye lens, thereby permitting the taking of pictures when the focus of said camera matches the instantaneous refractive power of the eye being tested. Thus, according to the patent, such eye examinations enable a physician to judge the condition of a patient's vascular system and, in addition, may facilitate his determining the presence of brain tumors, certain systemic disorders, and/or disorders of the eye and the retina thereof.

Of course, there are eye testing instruments presently in existence which require the dilation of the eye pupil by means of drugs in order for them to be operationally effective or optimized; however, they are so numerous that they are already well known in the art.

The aforementioned prior art devices are quite satisfactory for many practical purposes; nevertheless, the search for eye testing instruments that will constitute an improvement thereover—even for some specific purpose—goes on.

SUMMARY OF THE INVENTION

For some practical purposes, the subject invention constitutes an advancement in the eye testing instrument art. For instance, the invention is an improved eye testing instrument that includes an infrared light optical system combined with a flash lamp optical system for maintaining a dark room eye dilation condition during both the visual examination and the photographing thereof. In addition, in combination with the latter is another low level red optical element which facilitates the fixation of the eye being tested, so that it may be examined with respect to a predetermined reference position. Of course, of some considerable significance, is the fact that eyes—and especially the retinas thereof—may be examined and displayed without the use of drugs or other medication as the pupil dilation means.

Therefore, an important object of this invention is to provide an improved eye examination system.

Another of object of this invention is to provide an improved method and means for examining the retinas of human eyes without using drugs to dilate the pupils thereof.

Still another object of this invention is to provide a safe eye testing instrument, in that the person whose eyes are being tested is not visually incapacitated as a result of the testing thereof.

A further object of this invention is to provide an improved eye testing instrument which permits a person whose eyes have been tested therewith to return to work without loss of time, to drive an automobile with safety, and otherwise act or function without being adversely affected thereby.

A further object of this invention is to provide an improved method and means for testing and photographing the retinas of human eyes without injury, pain, or discomfort to the person whose eyes are being tested.

Another object of this invention is to provide an improved eye examination system which will not precipitate glaucoma or mydriasis as a result of the use thereof.

Another object of this invention is to provide an eye examination instrument which facilitates effecting the preliminary set-up procedure for the taking of color photographs of eye retinas.

Still another object of this invention is to provide an improved eye examination system which permits the display of the eyes being tested at a predetermined monitoring station, either nearby or remote.

Other objects and many of the attendant advantages of this invention will be readily appreciated as the same becomes better understood by reference to the following detailed description, when considered in connection with the accompanying drawing wherein:

DESCRIPTION OF THE PREFERRED EMBODIMENT

Figure 1:
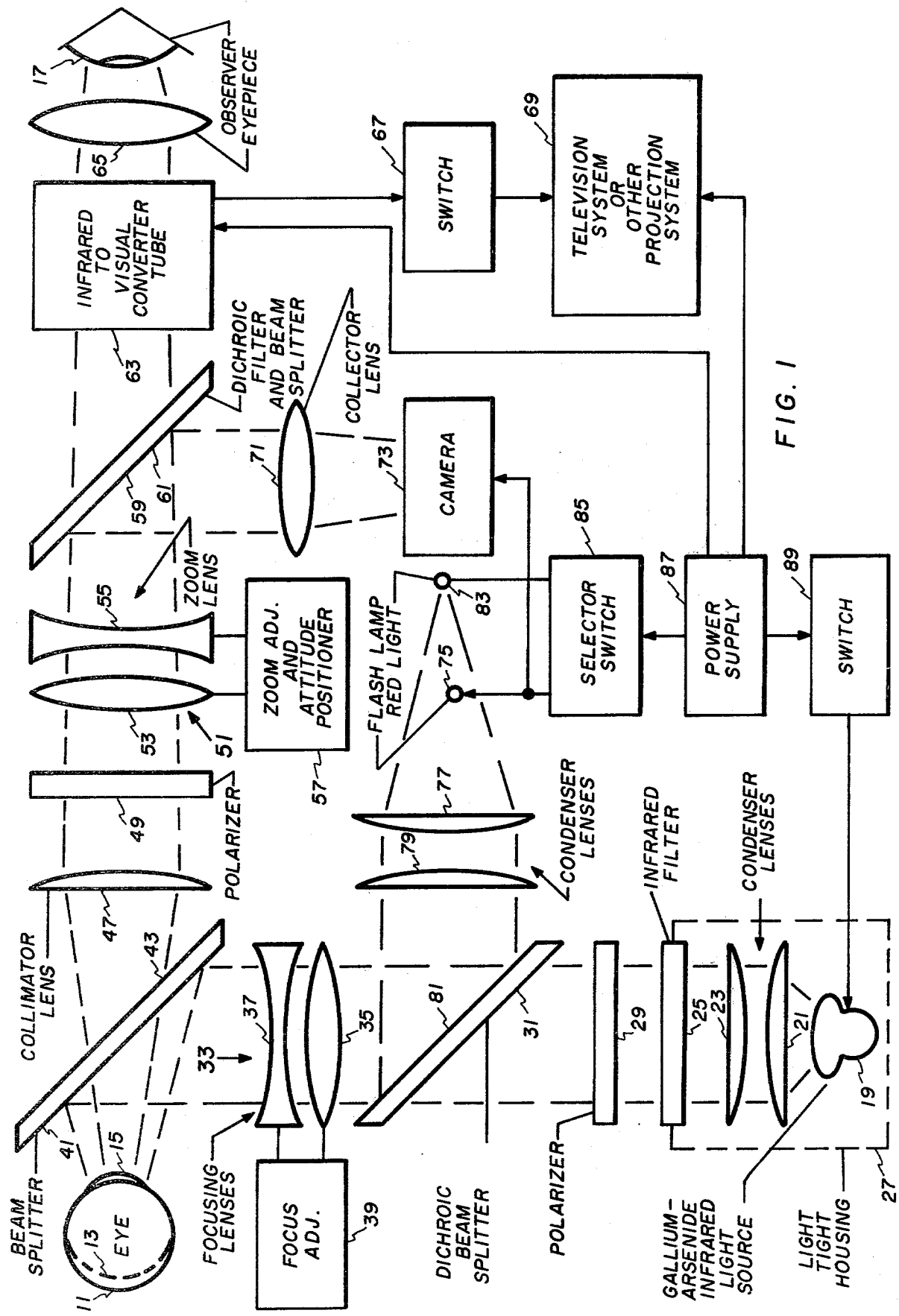
FIG. 1, the sole FIGURE in this case, illustrates in optical schematic and block diagram form the system constituting the instant invention.

Referring now to FIG. 1, there is shown an eye 11 of a human being (or other animal), having a retina 13 and a dilatable pupil 15, which is being tested or examined (or perhaps being otherwise operated upon in some manner) by an observer 17 using directed—and perhaps ambient—infrared light as the illumination means therefor, so that pupil 15 thereof will remain dilated during the examination thereof.

In order to simplify the disclosure of this invention, the aforementioned observer 17 will be considered to be a human observer; nevertheless, other sensors, devices, or instruments may be substituted therefor, in the event so doing happens to be warranted by operational circumstances. Of course, if such things should be substituted for observer 17, their design would have to be such that the optical entrance thereof would be compatible with the optical exit of the subject invention. Obviously, so doing would be well within the purview of the artisan having the benefit of the teachings presented herewith.

In order for eye 11, and especially retina 13 thereof, to be examined in an optimum manner, it must be properly illuminated by a light that does not interfere with pupil dilation and, yet, provides sufficient light to be readily visible to observer 17. It has been found that infrared light is quite satisfactory for such purpose; hence, a gallium arsenide light source 19 is used as the source thereof, and the infrared radiant energy produced thereby is then directed in such manners along first and second optical paths as to be appropriately received by retina 13 through pupil 15 of eye 11.

Spatially disposed along the aforesaid first optical path from infrared light source 19 and effectively downstream therefrom is a pair of condenser lenses 21 and 23, and spatially disposed downstream therefrom is an infrared filter 25. In conjunction with filter 25 is a light tight housing 27 which, although schematically illustrated herein, is constructed to prevent infrared light from escaping to the ambient environment, except through infrared filter 25, and thus it is directed along said first optical path.

Along said first optical path and downstream from said infrared filter 25 is a manually or otherwise rotatable but normally horizontally polarized polarizer 29, and disposed downstream therefrom is a dichroic beam splitter 31, with the attitude of the plane thereof being such that a predetermined angle—depicted as being substantially 45°, in this particular preferred embodiment—is formed with the axis of said first optical path for reasons which will be discussed more fully subsequently. Also disposed along and downstream from beam splitter 31 is a pair of focusing lenses 33—one positive lens 35 and one negative lens 37 compatible therewith—which are adapted for being relatively adjusted along the axis of said first optical path in such manner as to properly focus the infrared light traveling therealong as desired by a focus adjustment 39, the latter of which may be manual or otherwise.

Another beam splitter 41 is angularly disposed with the axis of said first optical path. In this case, it is illustrated as having its plane positioned at approximately 45° with said first optical path axis, but, of course, other angles could be used therefor. Moreover, beam splitter 41 is not only disposed at a 45° angle with the axis of said first optical path, it also makes substantially a 45° angle with a second optical path, the axis of which extends between the center of eye 11 and observer eye 17, thereby making the angle between said first and second optical paths be substantially 90°. As may readily be seen from FIG. 1, beam splitter 41 has a reflective surface 43 on one side thereof (as shown, on the underside thereof) which causes the infrared light and whatever other radiant energy is received thereby (from a source to be defined later) to be directed along said second optical path through pupil 15 of eye 11.

Also located along said second optical path and downstream from both eye 11 and beam splitter 41 is an aspheric field collimator lens 47 that is corrected for gallium arsenide wavelengths, and disposed downstream therefrom is a manually or otherwise rotatable but normally vertically polarized polarizer 49, and spatially disposed therefrom thereon is a zoom lens 51 consisting of a positive lens 53 and a complementary negative lens 55 that are relatively adjustable along the axis of said second optical path by a zoom adjustment and attitude positioner 57. Disposed downstream from zoom lens 51 is a dichroic filter and beam splitter 59 having a semi-mirrored, light reflective surface 61, with the angle of the plane thereof being such that it makes substantially a 45° angle with respect to the axis of said second optical path and thus forms a third optical path as a result of the reflection of radiant energy therefrom which, in turn, makes substantially a 90° angle with said second optical path.

An infrared to visual converter tube 63 is spatially located along said second optical path and downstream from the non-reflective surface of beam splitter 59. Infrared to visual converter tube 63 is, of course, well known, conventional, and commercially available from FJW Industries of Mount Prospect, Ill, as evidenced by the advertisement thereof in the upper left-hand corner of page 31 of the March, 1977, issue of Optical Spectra. In effect, at the optical output thereof, it provides a visual image of an object which has been illuminated by infrared energy upon which it is sighted—in this case, retina 13 of eye 11. It also produces an electrical output signal which represents whatever infrared energy signal (or image, or pattern, etc.) is received at the optical input thereof—likewise, in this particular case, retina 13 of eye 11.

Spatially disposed downstream of the optical output of the aforesaid infrared to visual converter tube 63 and along said second optical path is an eyepiece lens 65, and it is through this eyepiece lens that the eye (or sensor) of observer 17 looks, in order to observe the inside—and especially the retina—of eye 11.

The electrical output of infrared to visual converter tube 63 is connected through a switch 67 to any television system or other projection system 69 that would be compatible therewith and would display eye 11 in such manner—with respect to size, color, detail, location, etc.—that, say, an audience of people could observe eye 11 along with observer 17.

To this point, the emphasis with respect to the application of the instrument consituting this invention has been placed on the visual examination of human eyes. However, by now, it should be obvious to the artisan that numerous other objects could be so examined to an advantage and, hence, the application thereof is—or with minor design changes could be made to be—practically unlimited. Therefore, it should be understood that this disclosure is intended to be without limitation, but the preferred embodiment of the invention disclosed herein is slanted toward testing the human eye, especially since pupil dilation problems are involved therein.

In order to preserve the image of eye 11 at any given instant, it has been found that it is necessary to take color photographs thereof. Accordingly, in conjunction with beam splitter 59, a collector lens 71 and an electrically triggered camera 73 are spatially disposed therefrom along a third optical path, the latter of which is located such that it makes substantially a 90° angle with the aforementioned second optical path due to the substantially 45° angular dispositions of beam splitter 59 with respect to both of said second and third optical paths. But, in order to take bright, high resolution photographs, camera 73 requires that eye 11 be illuminated with a bright white light of the kind generated by a flash lamp; thus, a flash lamp 75 is spatially disposed in such manner as to direct its bright light flash through a pair of condenser lenses 77 and 79 and along a fourth optical path toward beam splitter 31 and especially to the semi-mirrored side 81 thereof, so that it may be reflected therefrom and the mirrored side 43 of beam splitter 41 and on into eye 11.

As will be discussed more fully below in conjunction with the operation of the invention, a very small, low intensity, but nevertheless visible red spot light 83 is also disposed along said fourth optical path at a distance from lens 77 that is approximately twice that the aforesaid flash lamp 75 is disposed therefrom. Although flash lamp 75 and red light 83 are both located on the same fourth optical path, they should be located in such contiguous manner therewith and also with respect to one another that flash lamp 75 does not interfere with the visibility of red light 83, as far as eye 11 is concerned. Red light 83 is adapted for constantly being lighted during the eye examination; however, it may optionally be turned off by selector switch 85 at the very instant a photograph is taken, if so desired.

Due to the transmission of the dull red spot of light 83 by condenser lenses 77 and 79, beam splitter 31, focusing lenses 35 and 37, and beam splitter 41, said red spot is seen by eye 11. Thus, it may be used as a reference fixation point by said eye 11, so that it may be easily, conveniently, comfortably, and effectively held in substantially the same place all of the time the retina thereof is being visually examined, as well as during or immediately up to the time it is photographed, in the event a photograph thereof is taken.

As is customary in the photography arts, camera 73 and flash lamp 75 are triggered simultaneously; therefore, the electrical trigger inputs thereof are interconnected and connected to one of the electrical outputs of a selector switch 85, the other electrical output of which is connected to the aforesaid red lamp 83. A power supply 87 has one of its electrical outputs connected to the input of selector switch 85 for supplying electrical energy thereto. Power supply 87 also may optionally be connected to appropriate inputs of the aforementioned infrared to visual converter tube 63 and television system or other projection system, too, unless it is desired to supply electric energy thereto from other suitable external sources for reasons of convenience, in the event either one or the other or both happen to be located at some distance remote therefrom. Obviously, the artisan could easily select whatever power supplies as would facilitate the operation of the invention for its intended purpose at any given time. On the other hand, the whole instrument constituting this invention could be made self-sufficient, self-contained, and portable by selecting whatever power supply as would be appropriate for power supply 87—be it battery, electric generator, or the like. Of course, the usual house electrical power source could be used therefor, too.

One of the electrical outputs of power supply 87 is connected through a switch 89 to the aforesaid gallium arsenide infrared light source 19 for timely effecting the electrical energization thereof.

Obviously, all of the above mentioned elements which make up this invention would have to be relatively supported by some appropriate mounting means; however, since such means is conventional in the optical art, the constructional design thereof has been left to the choice of the artisan.

Although numerous designs and relative dispositions of the various and sundry optical elements shown in FIG. 1 could be used, without limitation with respect thereto, the following representative ones are presented:

Lenses 21 and 23 form a condenser pair having approximately 4 inches effective focal length; and, thus, infrared light source 19 is located at the focal point thereof, so that the infrared light thereof becomes collimated.

Lenses 35 and 37 form a variable focus pair, with separate effective focal lengths of +2 inches and −2 inches, respectively. These focusing lenses are used to focus gallium arsenide infrared light source 19 into pupil 15 of eye 11 located approximately 4 inches away.

Dichroic beam splitter 31 may be located at any preferred design choice location between condenser lens 23 and focusing lens 35.

Infrared filter 25 may be located at any preferred design choice location between condenser lens 23 and beam splitter 31.

Polarizer 29 is rotatable but preferably a horizontal polarizer that may be located at any preferred design choice location between infrared filter 25 and beam splitter 31.

Lenses 77 and 79 have a combined focal length of 4 inches and are located approximately 12 inches from lens 35.

Flash lamp 75 is located about 4 inches from condenser lens 77 at about the focal point thereof.

Red spot light 83 is located about 8 inches from lens 77, so that it is reimaged about 4 inches from lens 35, the latter of which, in conjunction with lens 37, causes the red light therefrom to be collimated, thereby making it appear to be a tiny red spot located at infinity, as far as eye 11 is concerned. Hence, fixation thereon thereby is facilitated.

Lens 47 is an aspheric field lens—corrected for gallium arsenide and visible wavelengths—that has a focal length of approximately 3 inches; therefore, it is located on said second optical path about 3 inches from retina 13 of eye 11.

Polarizer 49 is preferably a rotatable but normally vertical polarizer that is located on said second optical path at any convenient design choice distance from lens 47.

Lenses 53 and 55 constitute zoom lens 51, the effective focal length (EFL) of which may vary from 2 to 8 inches, thereby permitting it to be located between polarizer 49 and beam splitter 61 at any design choice position along the aforesaid second optical path that will permit the focusing thereof on infrared to visual converter tube 63 with infrared light, and on camera 73 with visible light, via collector lens 71, the focal length of which is compatible with the distance camera 73 is from beam splitter 59.

Eyepiece lens 63 has a focal length of about 2 inches, and, hence, it is located along said second optical path about 2 inches from the exit of infrared to visual converter tube 63.

Again, for purposes of emphasis, the above dimensions, focal lengths, and optical element characteristics, etc., are merely representative; consequently, other design choices may be selected therefor by the artisan which will cause the subject invention to be optimized for any given operational circumstances without violating the spirit or scope of this invention. So doing, of course, would be well within the purview of said artisan, if he had the benefit of the teachings presented herewith.

MODE OF OPERATION

The operation of the invention will now be discussed briefly in conjunction with FIG. 1, the sole FIGURE of the drawing.

As previously indicated, it is standard procedure to dilate the eyes with medication and drugs for the purpose of facilitating the examination of the inside thereof, including the retina. And with increased use of lasers and other high intensity light sources, retinal examinations and photographs will be needed in the future more than ever for implementation of safety programs and for the maintenance of up-to-date medical records. Unfortunately, as previously suggested, most of the methods used heretofore for such purpose have a number of shortcomings from the patient's point of view, in that safety factors are usually involved. For example, if a person needs to drive a car, work, or otherwise be active in situations where it would be necessary for him to see well, it would be unsafe for him to do so while his vision was impaired as a result of his eyes having been dilated with drugs for examination purposes. Moreover, there appears to be at least an outside chance that mydriasis may precipitate glaucoma in those persons with the tendency toward it. And, in addition, there is the unnecessary discomfort and inconvenience caused by the use of a mydriatic. Accordingly, the subject invention may be used to an advantage whenever it is substituted for optical equipment operating in the visible spectrum because, for the most part, it operates in the infrared range, which does not cause the pupil to contract and close.

Immediately prior to the physical examination of the eyes, the person whose eyes are being examined remains in a dark room or a room where only a small red light is present, so as to permit the normal dilation of his eyes to occur, thereby, in turn, permitting a better observation thereof. Once dilated, the eye being tested is examined. Assuming that the eye being tested in this particular case is eye 11 and it is being examined by observer 13 after it has been put into a dilated state, then it, including retina 13 thereof, is properly illuminated by the infrared light traveling along the aforementioned first optical path from and through gallium arsenide infrared light source 19, condenser lenses 21 and 23, infrared filter 25, polarizer 29, beam splitter 31, focusing lenses 35 and 37, and redirecting beam splitter 41, respectively.

Said eye illuminating infrared light is then reflected from retina 13, after which it passes through beam splitter 41 and then travels along the aforesaid second optical path where it passes through collimator lens 47, polarizer 49, zoom lenses 53 and 55, dichroic filter and beam splitter 59 to infrared to visual converter tube 63, where it is converted to visible light thereby. Of course, that infrared image of eye 11 which occurred at the entrance of converter tube 63 then becomes a comparable visible image that is passed through eyepiece 65, where it may be viewed by observer 17, the eye examiner.

In order to optimize the image of eye 11 from the observer's point of view, several adjustments are available thereto. For instance, observer 17 may focus lenses 35 and 37 in such manner by means of conventional focus adjustment 39, so as to effectively concentrate as much infrared light (and/or other light or radiant energy) on retina 13 as possible. Also, polarizer 29 may be rotated or otherwise positioned to prevent as much glare as possible. And, if so desired, the amount of infrared light generated by gallium arsenide light source 19 may be adjusted by controlling the electrical energy supplied thereto by regulatable power supply 87. Furthermore, the amount of infrared light (and/or other light or radiant energy) reflected from retina 13 may be controlled by adjusting polarizer 49—which may, in fact, be adjusted in conjunction with the adjustment of polarizer 29—and zoom lenses 53 and 55 by means of zoom adjust and attitude positioner 57. Of course, infrared to visual converter tube 63 has had an adjustment means inherently incorporated therein during construction by the commercial manufacturer thereof, and, thus, it, too, may be adjusted as desired by operator 17.

Being a semi-mirror type of beam splitter, dichroic filter and beam splitter 59 reflects a portion of whatever light or other radiant energy is received thereby toward collector lens 71 and camera 73. Hence, if so desired, infrared pictures of eye 11 may be taken thereby. In addition, camera 73 may be used to take black and white and color pictures of eye 11, if such is warranted by operational and examination circumstances. However, to facilitate doing the latter, it becomes necessary to illuminate the inside of eye 11 with a white light. Of course, the illumination thereof must be done almost instantaneously, in order to prevent automatic pupil closure in response thereto. For such purpose, flash lamp 75 is used, and it and camera 73 are actuated timely and simultaneously by triggering selector switch 85. When energized, flash lamp 75 generates a very bright white light which travels down the aforesaid fourth optical path through condenser lenses 77 and 79, after which it is reflected by semi-mirror surface 81 of dichroic beam splitter 31, and so on, so as to travel to eye 11 for the illumination thereof thereby. The reflected white light from eye 11 travels down the aforementioned second optical path to beam splitter 59, where it is redirected through collector lens 71 to camera 73. Because camera 73 and flash lamp 75 are synchronized as is conventional in the photographic art, whatever film has been loaded in camera 73 will be timely exposed as the flash of lamp 75 occurs, thereby taking a picture of the inside of eye 11 at that time before the pupil thereof has had time to react thereto and close. As a matter of fact, the pupil dilation of eye 11 is ordinarily not adversely affected by this photo procedure, due to the exceedingly short period of time that eye 11 is subjected to the white light from flash lamp 75; therefore, as a general rule, the eye examination may be continued even after a photograph has been taken thereof.

During both the infrared examination period and the photographing time, it is definitely desirable that retina 13 of eye 11 be held at some particular reference position (or moved in some predetermined manner with respect thereof). Hence, one of the key advantages of this invention is effected by the presence of tiny infrared or red light 83 which is present physically in contiguous disposition with the aforesaid fourth optical path. A very small amount of red light from light 83 illuminates eye 11, and retina 13 thereof; hence, it can constantly be seen by the eye 11 during the examination and photographing thereof. In other words, eye 11 may be sighted or fixed on tiny red light 83 and, thus, as previously suggested, be more easily held in a fixed position with respect thereto and to infrared to visual converter tube 63 and camera 73, regardless of how long the eye examination takes or how often it occurs.

On occasion, it may be advantageous for the image of eye 11 to be observed by a number of people or perhaps at some place remote from the position of the subject instrument discussed so far. In such case, the electrical analog signal representing the visual image of eye 11 produced by infrared to visual converter tube 63 may be supplied to television or other projection system 69 (via switch 67). Then eye 11 is displayed in such manner that the observer or observers would not have to look through a relatively small eyepiece, and both eyes of the observer could be used for the viewing thereof.

At this time, it would perhaps be noteworthy that each and every one of the elements shown in schematic and block diagram form in FIG. 1 is well known, conventional, and commercially available. Therefore, it is to be understood that it is their unique interconnections and optical or other interactions that effect the subject invention and cause it to produce the above stated improved results.

Obviously, many modifications and variations of the present invention are possible in the light of the above teachings. It is, therefore, to be understood that within the scope of the appended claims the invention may be practiced otherwise than as specifically described.

What is claimed is:

1. An eye examination instrument, comprising in combination:

means for projecting an infrared light along a first optical axis;

means spatially disposed from said infrared light projecting means along said first optical axis for receiving and passing therethrough the infrared light therefrom along said first optical axis and for receiving and redirecting a red light from along a second optical axis in such manner that it, too, will be directed along the aforesaid first optical axis with some degree of coincidence with the aforesaid infrared light;

means spatially disposed from said receiving, passing, and redirecting means and in contiguous disposition with said second optical axis for supplying said red light thereto;

means spatially disposed from the aforesaid receiving, passing, and redirecting means along said first optical axis for receiving and redirecting said infrared light received therefrom in a first predetermined direction toward the retina of an eye being examined that is positioned along a third optical axis, and for passing therethrough a portion of said redirecting infrared light that has been reflected from the retina of said eye back along said third optical axis in a second direction that is opposite the aforesaid first predetermined direction;

means spatially disposed between the aforesaid first and second mentioned receiving, redirecting, and passing means and along said first optical axis for directing the aforesaid infrared and red lights onto the pupil of said eye;

means spatially disposed downstream from said second mentioned receiving, redirecting, and passing means and along said third optical axis for receiving, redirecting, and passing therethrough portions of the aforesaid infrared light reflected from the retina of said eye;

means spatially disposed downstream from said last mentioned receiving, redirecting, and passing means and along said third optical axis for converting said retina reflected infrared light to a light image proportional thereto that would be visible to the human eye;

whereby the eye to be examined is permitted by the use of infrared light to attain and maintain full dilation, and will be focused at infinity on the source of said red light and held fixed thereon by the examinee without eye movement during the examination;

means spatially disposed from said first mentioned receiving, passing, and redirecting means and in contiguous disposition with said second optical axis for timely supplying a flash of bright white light thereto, including at least one optical member in said second optical axis between the source of said white light and said first mentioned receiving, passing, and redirecting means, wherein the source of said white light is about one-half the distance from said at least one optical member and the source of said red light, and said first and second mentioned receiving, passing, and redirecting means, said directing means, and said at least one optical member cooperate to collimate said red light and focus said white light on the pupil of said eye;

means spatially disposed from said third mentioned receiving, passing, and redirecting means and along a fourth optical axis for timely photographing the light redirected thereby; and means for selectively actuating the aforesaid white light supplying means and said photographing means simultaneously or separately in response to a predetermined trigger signal.

2. An eye examination instrument, comprising in combination:

an infrared light source adapted for projecting infrared light along a first predetermined optical path;

a first pair of condenser lenses spatially disposed downstream from said infrared light source along said first predetermined optical path;

an infrared filter spatially disposed downstream from said first pair of condenser lenses along said first predetermined optical path;

a first rotatable polarizer spatially disposed downstream form said infrared filter along said first predetermined optical path;

a beam splitter spatially disposed downstream from said first rotatable polarizer along said first predetermined optical path at a predetermined angle therewith;

a pair of focusing lenses spatially disposed downstream from said beam splitter along said first predetermined optical path;

a second beam splitter spatially disposed downstream from said pair of focusing lenses along said first predetermined optical path and at a predetermined angle therewith, the angle of which is such as will make the optical path of the eye to be examined to be a second predetermined optical path having a predetermined angle therewith;

a collimater lens spatially disposed downstream from said second beam splitter along said second predetermined optical path;

a second rotatable polarizer spatially disposed downstream from said collimator lens along said second predetermined optical path;

a pair of zoom lenses spatially disposed downstream from said second rotatable polarizer along said second predetermined optical path;

a third beam splitter spatially disposed downstream from said pair of zoom lenses along said second predetermined optical path and at a predetermined angle therewith;

an infrared to visual converter tube spatially disposed downstream of said third beam splitter along said second optical path;

an eyepiece lens contiguously disposed downstream from the optical output of said infrared to visual converter tube adapted for being viewed by a predetermined observer;

a collector lens spatially disposed from the upstream side of the aforesaid third beam splitter along a third predetermined optical path having a predetermined angle with the aforesaid second optical path;

a camera spatially disposed downstream from said collector lens along said third optical path;

a flash lamp spatially disposed from the downstream side of the aforesaid first beam splitter and in contiguous disposition with a fourth optical path;

a second pair of condenser lenses spatially disposed between said flash lamp and the downstream side of said first beam splitter along said fourth optical path;

a red spot light spatially disposed upstream from said second pair of condenser lenses and in contiguous disposition with said fourth optical path, and about twice the distance from said second pair of condenser lenses as said flash lamp; and means effectively connected to said flesh lamp and the aforesaid camera for timely effecting the synchronized actuation thereof in response to a predetermined trigger signal.

3. The invention of claim 2, further characterized by a light tight housing surrounding said infrared light source, said first pair of condenser lenses, and said infrared filter in such manner as to permit the infrared light from said infrared light source to be projected through said condenser lenses and said infrared filter along said first predetermined optical path.

4. The device of claim 2, further characterized by means connected to said pair of focusing lenses for effecting the adjustment thereof.

5. The invention of claim 2, further characterized by means connected to said pair of zoom lenses for effecting the zoom adjustment and attitude position thereof.

* * * * *